United States Patent [19]

Dowdy

[11] Patent Number: 5,074,316
[45] Date of Patent: Dec. 24, 1991

[54] BRACHIAL ANGIOGRAPHY SURGICAL DRAPE

[75] Inventor: Richard C. Dowdy, Valencia, Calif.

[73] Assignee: Baxter International Inc., Deerfield, Ill.

[21] Appl. No.: 732,732

[22] Filed: Jul. 18, 1991

Related U.S. Application Data

[63] Continuation of Ser. No. 491,911, Mar. 12, 1990, abandoned.

[51] Int. Cl.$^5$ .............. A61B 19/00; A61B 19/08
[52] U.S. Cl. .................... 128/849; 128/852; 128/853
[58] Field of Search ................. 128/849-856

[56] References Cited

U.S. PATENT DOCUMENTS

| | | | |
|---|---|---|---|
| Re. 27,710 | 7/1973 | Melges | 128/852 |
| 1,724,443 | 8/1929 | Wheeler | 128/849 |
| 3,260,260 | 7/1966 | Questel | 128/851 |
| 3,452,750 | 7/1969 | Blanford | 128/853 |
| 3,503,391 | 3/1970 | Melges | 128/852 |
| 3,667,458 | 6/1972 | Krebs | 128/853 |
| 3,721,234 | 3/1973 | Hadtke | 128/852 |
| 3,738,359 | 6/1973 | Lindquist | 128/852 |
| 3,791,382 | 2/1974 | Collins | 128/853 |
| 3,826,253 | 7/1974 | Larsh et al. | 128/854 |
| 3,856,006 | 12/1974 | Krzewinski | 128/852 |
| 3,871,369 | 3/1975 | Krzewinski | 128/853 |
| 3,881,474 | 5/1975 | Krzewinski | 128/852 |
| 3,882,859 | 5/1975 | Ericson | 128/854 |
| 3,921,627 | 11/1975 | Wilson | 128/853 |
| 4,033,341 | 7/1977 | Scrivens | 128/852 |
| 4,040,418 | 8/1977 | Collins | 128/852 |
| 4,051,845 | 10/1977 | Collins | 128/855 |
| 4,275,719 | 6/1981 | Mayer | 128/849 |
| 4,476,860 | 10/1984 | Collins | 128/852 |
| 4,553,538 | 11/1985 | Rafelson | 128/852 |
| 4,586,498 | 5/1986 | Morris | 128/853 |
| 4,596,245 | 6/1986 | Morris | 128/852 |
| 4,598,458 | 7/1986 | McAllester | 128/853 |
| 4,664,103 | 5/1987 | Martin et al. | 128/852 |
| 4,859,527 | 8/1989 | DiStefano | 128/849 |
| 4,873,997 | 10/1989 | Marshall | 128/849 |

Primary Examiner—Robert A. Hafer
Assistant Examiner—Michael Brown
Attorney, Agent, or Firm—Kay H. Pierce; Paul C. Flattery

[57] ABSTRACT

A surgical drape for use in surgical procedures such as those wherein a catheter is inserted within a vein or artery of a patient. The drape includes a base sheet, for covering portions of the patient, that includes a fenestration and at least one tab portion that provides a member to which a catheter, inserted in a vein or artery of a patient, can be removably coupled during the surgical procedure. The drape further includes a pleated sheet portion so constructed and arranged so as to drape along the patient's arm near the operative site. In an embodiment, the drape includes an instrument pouch. The instrument pouch can be removably secured to the drape near the operative site. The pouch includes means for removably receiving surgical tools and positioning catheters used during the surgical procedure with respect to the drape. Preferably, the pouch is substantially transparent.

7 Claims, 3 Drawing Sheets

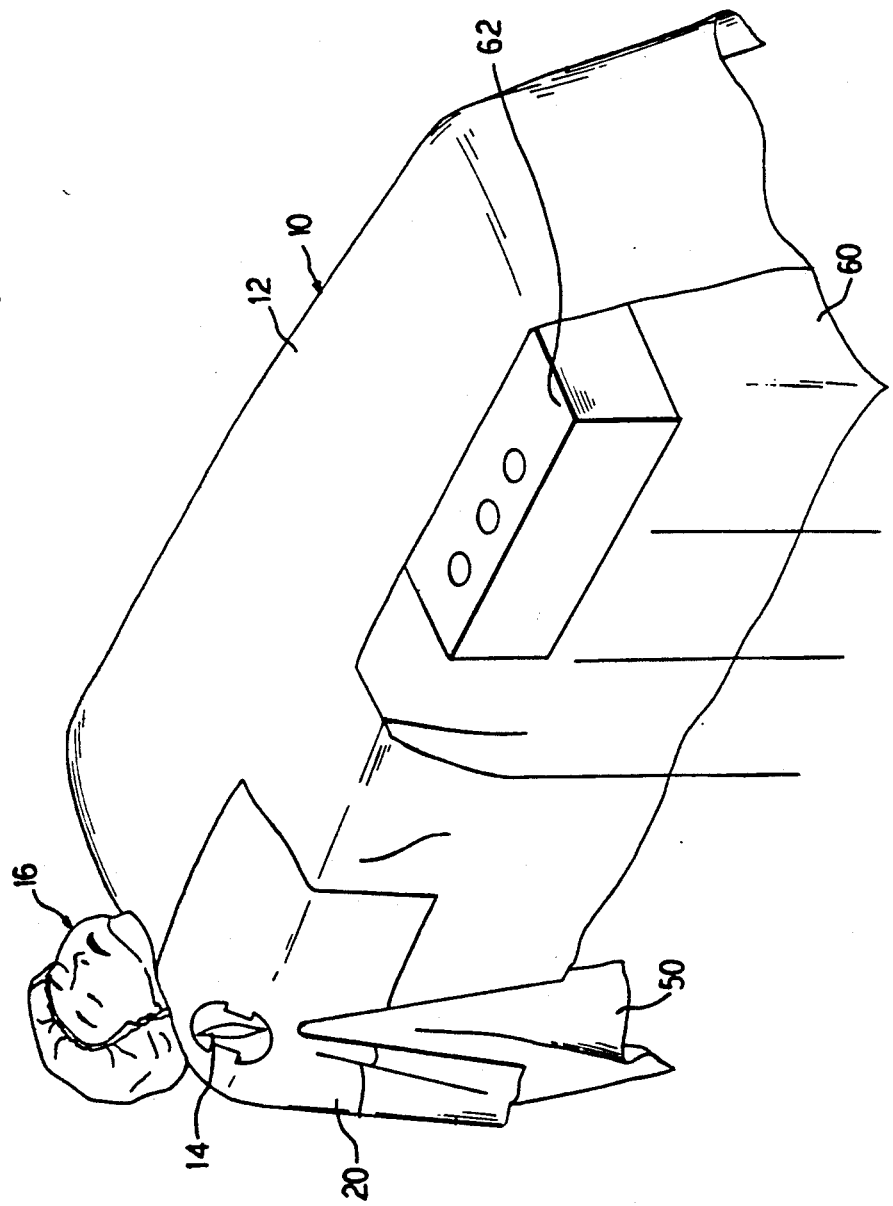

BRACHIAL ANGIOGRAPHY SURGICAL DRAPE

This is a continuation of application Ser. No. 7/491,911, filed on Mar. 12, 1990 now abandoned.

BACKGROUND OF THE INVENTION

The present invention relates generally to surgical drapes. More specifically, the present invention relates to surgical drapes for use in procedures that include the insertion of a catheter into a vein or artery of a patient.

There are a variety of different surgical drapes that are available. Surgical drapes are used, in part, to provide a sterile field during the surgical procedure. Although some surgical drapes are designed for specific surgical procedures, certain surgical procedures still require surgical personnel to modify or adapt available surgical drapes in an attempt to create a viable drape.

Cardiac catheterization and angiography procedures are surgical procedures that, due to their nature, present special requirements for a surgical drape. Cardiac catheterization is the introduction of a catheter (a long slender tube) into the heart in order to obtain information about the structure and function of the heart, the cardiac valves, the coronary arteries, and the like. The catheter is typically introduced through an artery or vein.

Typically, the catheter is introduced through the brachial artery to determine the pressure within the heart, determine abnormalities in the structure of the heart, and the like. A typical direct brachial approach is performed by a transverse incision made at the top of a patient's right arm. During the surgical procedure, the catheter is manipulated by the surgeon through the artery into the heart.

There are other similar surgical procedures wherein a catheter or the like is inserted through an artery or a vein, such as, for example, direct percutaneous femoral procedures.

Currently, disposable, non-woven and reusable woven surgical drapes are used to create a sterile field for cardiac catheterization and angiography procedures. Typically, two or more surgical drapes are utilized to provide such a sterile field. The surgical drapes are utilized in conjunction with a smaller aperture drape that is superimposed over a point of catheter entry on the patient. For example, a surgical drape set up for a cardiac catheterization procedure would be two ¾ sheets, two ½ sheets, and an additional draping applied to cover up possible gaps. Presently, drapes are spliced together at the operative site, or some other place on the sterile field. Catheter clips are anchored to tie off arteries and the surgeon attempts, to the extent possible, to position them at various places on the drape.

Of course, the fact that currently available surgical drapes require the use of multiple drapes during cardiac catheterization and angiography procedures presents a number of problems and concerns. Furthermore, the use of a multiple number of drapes presents excess draping that may interfere with the surgeon and other surgery personnel during the. surgical procedure. Moreover, problems are encountered with typical surgical drapes due to the fact that catheters must be inserted within the artery, maintained in position, and manipulated by the surgeon during the procedure.

An additional concern with respect to the use of surgical drapes during these types of surgical procedures is the ability of surgical personnel to view the instrumentation console. Still further, a concern with a typical surgical drape, is the ability of the surgeon to position surgical equipment near the operative site.

There is therefore a need for an improved surgical drape directed to procedures such as those wherein a catheter is inserted in a vein or artery of a patient.

SUMMARY OF THE INVENTION

The present invention provides an improved surgical drape for use in surgical procedures such as those wherein a catheter is inserted within a vein or artery of a patient.

In an embodiment of the surgical drape of the present invention, the drape comprises a base sheet, for covering portions of the patient, that includes a fenestration and at least one tab portion is located in juxtaposition to the fenestration. The tab portion provides means to which a catheter, inserted in a vein or artery of a patient, can be removably coupled during the surgical procedure. Preferably, at least two tabs are located on opposite sides of the fenestration. In a preferred embodiment, the base sheet includes a reinforcement panel, a portion of which has been removed to define an aperture that corresponds to the fenestration, and the tab is constructed from a material used to create the reinforcement panel.

In a further embodiment of the surgical drape, the drape includes a base sheet portion for covering at least a substantial portion of a patient's body. The base sheet portion includes a fenestration for providing access to an operative site on a patient. The drape further includes a pleated sheet portion so constructed and arranged so as to drape along the patient's arm near the operative site.

In another embodiment of the surgical drape of the present invention, the drape includes a base sheet having a fenestration for providing access to an operative site on a patient and an instrument pouch. The instrument pouch includes means for removably securing the pouch to the drape near the operative site. The pouch includes means for removably receiving surgical tools and positioning catheters used during the surgical procedure with respect to the drape. Preferably, the pouch is substantially transparent.

In an embodiment of the surgical drapes of the present invention, the base sheet includes an adhesive area located on an underside thereof, that substantially circumscribes the fenestration, for securing the fenestration around an operative site on the patient.

In an embodiment of the surgical drapes of the present invention, the drape includes a substantially transparent portion located at an area remote from the fenestration.

In an embodiment of the surgical drapes of the present invention, the fenestration of the surgical drape has an elliptical shape.

₁ An advantage of the present invention is to provide an improved surgical drape for use in a surgical procedure wherein a catheter is inserted within a vein or artery of a patient.

A still further advantage of the present invention is that it provides a surgical drape for use in cardiac catheterization or angiography procedures.

Another advantage of the present invention is that it provides a surgical drape that eliminates the need for the use of additional surgical drapes during procedures, such as cardiac catheterization and brachial angiography.

Furthermore, an advantage of the present invention is that it provides a surgical drape that includes a pleated portion that allows the drape to be draped over a patient's arm and to be utilized with patients of differing sizes.

Further, an advantage of the present invention is that it provides a surgical drape that includes a pleated portion that allows the surgical drape to be utilized with patients of various sizes, but does not interfere with the surgeon performing the procedure.

Moreover, an advantage of the present invention is that it provides a surgical drape including tab portions that allow catheter lines to be secured near the entry of the incision in the patient to provide for greater control and use of the catheters by the surgeon throughout the course of the surgical procedure.

Still, an advantage of the present invention is that it provides an instrument pouch that assists in controlling the catheters that have been inserted in the patient while still allowing the surgeon to view the catheter lines.

Additionally, an advantage of the present invention is that it provides a surgical drape system including an instrument pouch that allows instruments to be located near an operative site where they can be easily accessed by the surgeon.

Another advantage of the present invention is that it provides a surgical drape including a transparent portion for allowing surgical personnel to easily view an instrumentation console.

Additional features and advantages of the present invention are described in, and will be apparent from, the detailed description of the presently preferred embodiments and from the drawings.

BRIEF DESCRIPTION OF THE DRAWINGS

FIG. 2 illustrates a perspective view of the surgical drape of the present invention positioned over a patient.

DETAILED DESCRIPTION OF THE PRESENTLY PREFERRED EMBODIMENTS

The present invention provides an improved surgical drape, the surgical drape is specifically directed for use in surgical procedures wherein a catheter is inserted into an artery or vein of a patient. Such procedures include cardiac catheterization and brachial angiography procedures. Of course, the surgical drape can be used during other surgical procedures, such as, for example, percutaneous femoral procedures.

Figure 1:
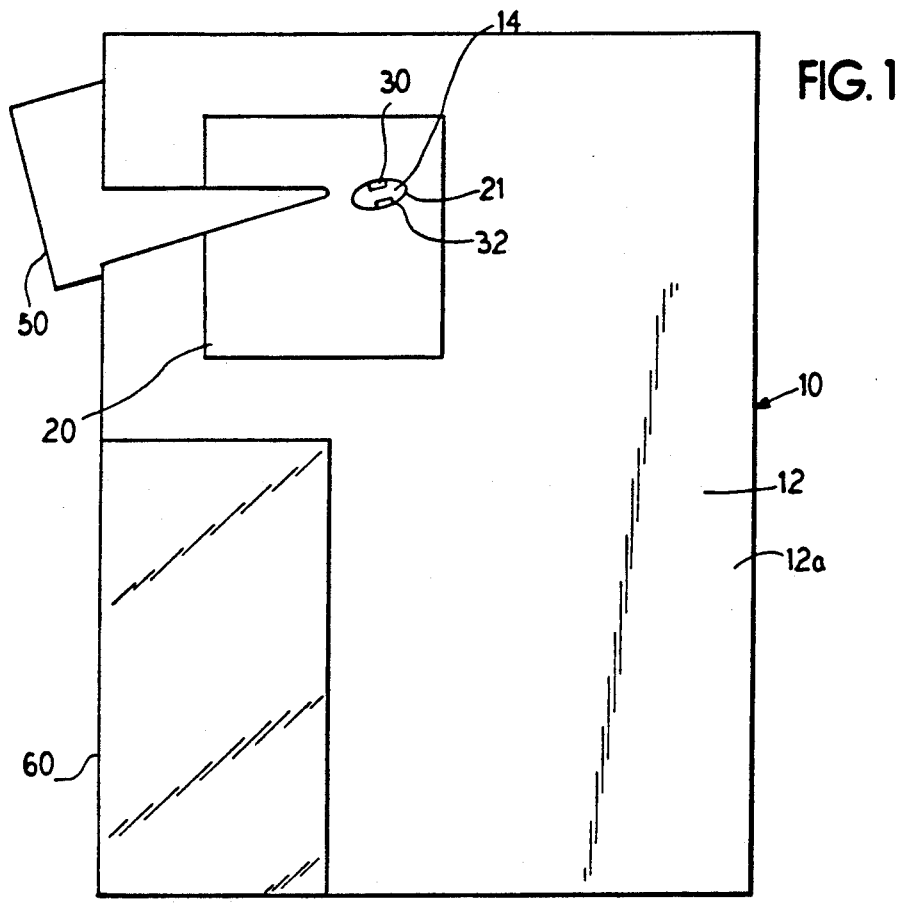
FIG. 1 illustrates a plan view of the surgical drape of the present invention.

Referring now to FIG. 1, the surgical drape 10 of the present invention is illustrated. The surgical drape 10 includes a base sheet 12 designed to cover at least a majority of a patient's body. Preferably, the base sheet 12 is constructed from a non-woven material fabric having a cellulose side/face 12a and a polyester side/face 12b. The polyester side/face 12b, of the surgical drape 10 contacts the patient when the drape is positioned over the patient. It has been found that a surgical drape 10 having a base sheet 12 of approximately 77 inches by 100 inches provides a surgical drape that is sufficiently large to cover at least a majority of a patient's body.

The surgical drape 10 includes a fenestration 14 or aperture that provides the surgeon with access to an operative site on a patient. As illustrated in FIG. 2, for use in brachial angiography and cardiac catheterization procedures, the fenestration 14 is so arranged and located on the surgical drape 10 that it is located at approximately the top of the right arm of a patient 16 when the drape is positioned on the patient. The fenestration 14 thereby provides the surgeon with access to an operative area in which a catheter can be inserted through the brachial artery. As illustrated, the fenestration 14 preferably has an elliptical, or oval, shape. It has been found that an elliptical fenestration that is approximately 3 inches in width and approximately 5 inches in length functions satisfactorily in cardiac catheterization procedures.

The surgical drape 10 includes a reinforcement panel 20. The reinforcement panel 20 affords moisture absorbency on the exposed surface face 12a of the drape 10. The reinforcement panel 20, in an embodiment, is constructed from ISO—BAC. However, the reinforcement panel 20 can be constructed from any absorbent non-woven reinforcement material. Preferably, the reinforcement material is a low linting, low abrasion, non-woven structure.

The reinforcement panel 20 is secured to the base sheet 12 and includes an aperture 21 that substantially corresponds to the fenestration 14 in the base sheet. To this end, the reinforcement panel 20 is secured to the cellulose face/side 12a that does not contact the patient of the base sheet 12.

Figure 4:
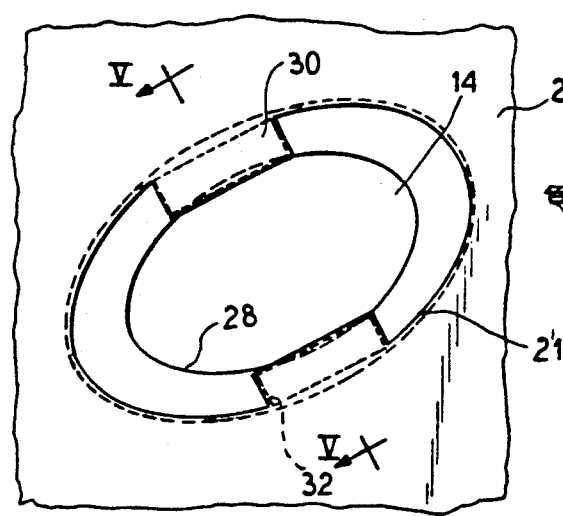
FIG. 4 illustrates a detailed view of a portion of the surgical drape of the present invention illustrating, in detail, the tab portions.

Referring now specifically to FIG. 4, a portion of the reinforcement panel 20 is illustrated. As illustrated, the reinforcement panel 20 defines two tabs 30 and 32, respectively, located on opposite sides of the aperture 21 in the reinforcement panel 20. In an embodiment of the present invention that has been found to function satisfactorily, the reinforcement panel 20 measures approximately 28 inches ±½ inch by 28 inches ±½ inch.

Figure 5:
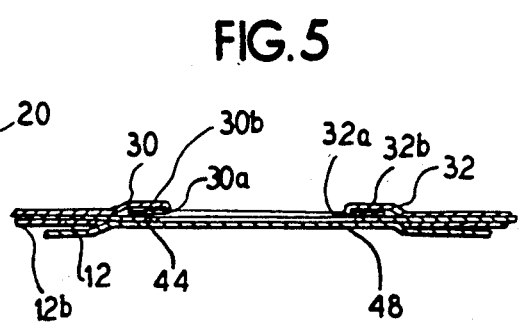
FIG. 5 illustrates a cross-sectional view of FIG. 4 taken along lines V—V of FIG. 4.

Referring now to FIG. 5, the tabs 30 and 32, in the reinforcement panel 20, are created by folding back an area of the reinforcement material around the aperture 21. Accordingly, the tabs 30 and 32 are created from the reinforcement material. The tabs 30 and 32, when so created, are defined by two layers 30a and 30b and 32a and 32b, respectively, of reinforcement material. To secure the two layers 30a and 30b, and 32a and 32b, of material together to define the tabs 30 and 32, a layer of two side tape or other adhesive means can be located therebetween. In an embodiment of the present invention, that has been found to function satisfactorily, the tabs 30 and 32 have a width of approximately two inches and a length of approximately ½ inch.

Figure 3:
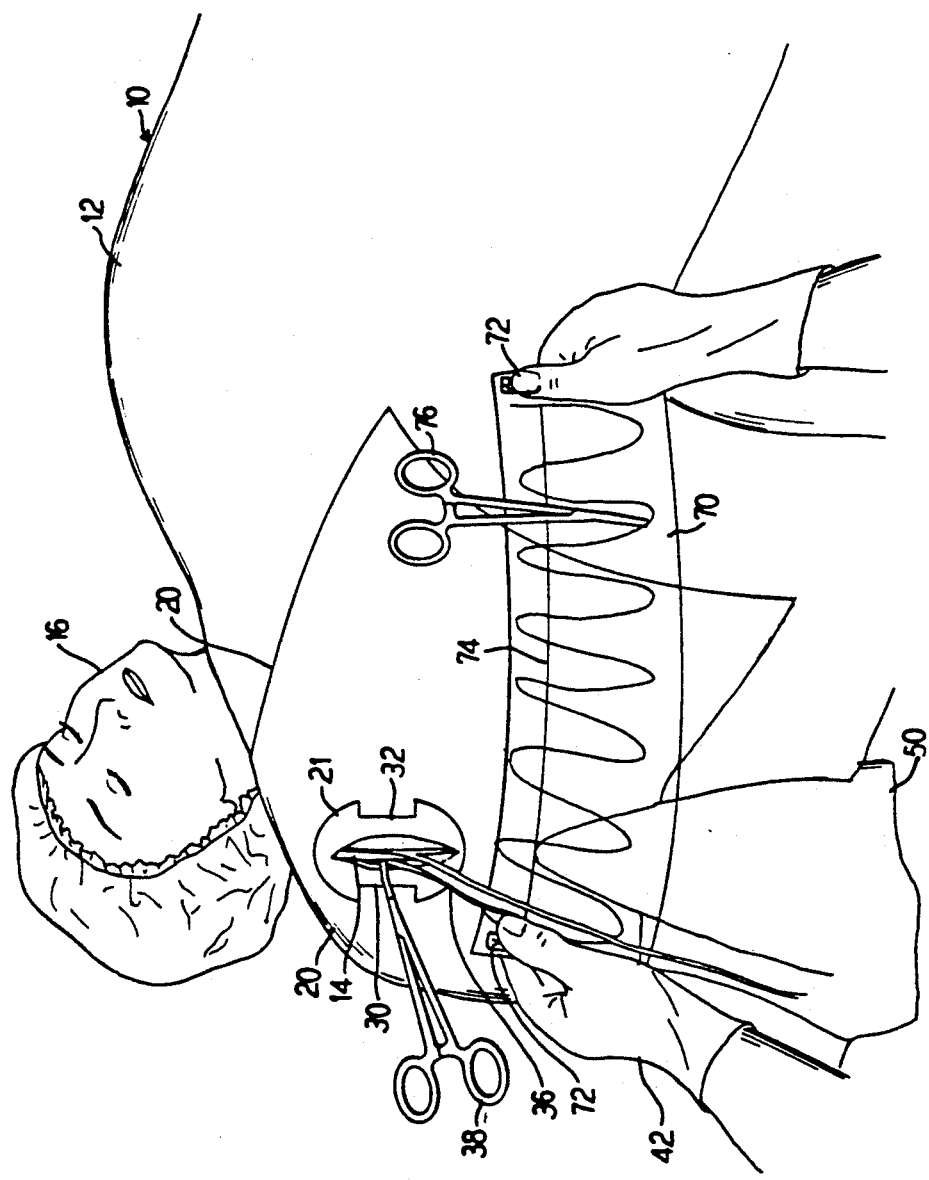
FIG. 3 illustrates a portion of the surgical drape system of the present invention positioned over the patient, and including an instrument pouch.

The tabs 30 and 32 protrude from the periphery of the aperture 21 in the reinforcement panel 20 partially into the fenestration 14 in the base sheet 12 when the reinforcement panel 20 is secured to the base sheet. The tabs 30 and 32 provide means for allowing catheter lines 36 to be secured to the surgical drape 10. To this end, as illustrated in FIG. 3, by using a clip instrument 38, the catheter line 36 can be secured to a tab 30, and thereby the surgical drape 10, removably securing the catheter to the drape near the operative site.

The use of the tabs 30 and 32 facilitates the entry and control of catheter lines and/or guide wires used during such procedures. Due to the location of the tabs 30 and 32 near or within a portion of the fenestration 14, the catheter lines 36 can be removably secured at the operative site. This provides the surgeon 42 with easy access during the surgical procedure. The fact that the tabs 30 and 32 are created from the reinforcement material of the reinforcement panel 20, and that this material is folded over to define the tabs, provides a sturdy thick tab to which clip instruments 38 can be secured. It should be noted that the tabs 30 and 32, in percutaneous femoral procedures can be used to anchor catheter sheaths.

Preferably, the surgical drape 10 includes an adhesive line 28 that circumscribes the fenestration 14. The adhesive line 28 allows the fenestration 14 to be secured around the operative site. The elliptical shape of the fenestration 14, and adhesive line 28 function to provide a seal around the catheter entry site and also prevents the adhesive from the patient's stitches that may have resulted from another procedure.

Referring to FIG. 5, the adhesive line 44, in the embodiment illustrated, is defined by a sheet of plastic having an aperture and adhesive on one side that is located between the reinforcement panel 20 and base sheet 12. The adhesive line 28 extends into and around the fenestration 14 in the base sheet 12.

To prevent the adhesive line 44 from sticking to itself or other portions of the drape 10 prior to use, a sheet of removable material 48 can be located over the adhesive line 28.

As illustrated in FIG. 1-3, the surgical drape 10 of the present invention includes a pleated section 50. As specifically illustrated in FIG. 2, the pleated section 50 is designed to cover at least the patient's arm during the surgical procedure. Due to its construction, the pleated section 50 allows the base sheet 12 to drape around a patient's arm at the catheter insertion site. The pleated section 50 of the surgical drape 10 of the present invention allows the drape to be easily adjusted with respect to the patient's size and type of procedure to be performed.

Preferably, the pleated section 50 is created in the surgical drape 10 as follows. The base sheet 12, as illustrated in FIG. 1, can include a substantially triangular cut-out portion 52. To create the pleated section 50, a rectangular panel of material, that will define the pleated section 50, is secured along one edge of the cut-out portion on the polyester side/face 12b. The rectangular sheet of material can be secured along the edge of the cut-out portion with an adhesive or other means for securing. The rectangular sheet is then folded over. A second side of the folded panel is then secured, with suitable adhesive; along a second edge of the triangular cut-out portion. This creates a pleated section 50 that will drape downwardly from a portion of the base sheet 12. It has been found that in an embodiment of the present invention, a rectangular panel having the dimensions of approximately 25 inches ±½ inch by approximately 36 inches ±½ inch functions satisfactorily to create the pleated section 50.

In the preferred embodiment of the surgical drape 10 illustrated, the surgical drape includes a transparent portion 60. The transparent portion 60 allows the surgical drape 10 to be positioned over an instrumentation console 62, as illustrated in FIG. 2, while still allowing the instrumentation console 62 to be viewed by the surgical personnel during the surgical procedure. The transparent portion 60 is preferably constructed from a substantially transparent plastic, for example, polyethylene. The transparent portion 60 can be secured to the base sheet 12 by a suitable adhesive or other means. It has been found that in a preferred embodiment that a transparent portion 60 having the dimensions of approximately 53 inches by about 26½ inches provides a resultant surgical drape 10 wherein the drape can be located in a proper position on the patient, with respect to the operative site and the instrumentation console 62 can be easily viewed by surgical personnel. The drape is so constructed and arranged that the transparent portion 60, although it covers the instrumentation console 62, because it is transparent, allows the console to be viewed by surgical personnel.

When the surgical drape 10, as illustrated in FIG. 2, is positioned over the patient, the reinforcement panel 20 is located over the right shoulder of the patient and the fenestration 14 is positioned so that it allows the surgeon to make a transverse incision at the top of the patient's right arm. As further illustrated in FIG. 2, the pleated section 50 of the surgical drape 10 allows the drape to drape and cover the right arm of the patient during such a procedure.

The surgical drape system of the present invention also includes an instrument pouch 70. The instrument pouch 70 preferably is transparent and includes means for securing same to the surgical drape 10. In the embodiment of the instrument pouch 70 illustrated, the instrument pouch 70 includes adhesive sections 72 that, preferably run vertically on the pouch 70, and allow the instrument pouch to be removably secured to the surgical drape 10.

The instrument pouch 70 is so constructed and arranged that it assists, as illustrated in FIG. 3, in securing the catheter lines 36 in position, with respect to the surgical drape. To this end, the instrument pouch 70 can be placed over the catheter lines 36. Because the instrument pouch 70 is transparent, it therefore allows the catheter lines 36 to be viewed during the surgical procedure. Due to its construction, the instrument pouch 70 allows the surgeon to easily manipulate the catheters as desired during the surgical procedure.

The instrument pouch 70 includes a plurality of instrument receiving pouches or sleeves 74. As illustrated, surgical instruments 76 can be received within the sleeves 74 of the instrument pouch 70 so that they are readily available at the operative site during the surgical procedure.

As previously stated, the instrument pouch 70 functions, in part, as an additional means for securing catheter lines 36, as well as retaining surgical instruments 76. To this end, the instrument pouch 70 is superimposed over the catheter lines 36 after the catheters have been inserted into the patient 16. This allows for placement by the surgeon and eliminates the need for threading catheter lines.

Preferably, the instrument pouch is constructed from a translucent plastic such as, for example, polyethylene. It has been found, in an embodiment of the present invention, that a instrument pouch 70 having a length of approximately 18 inches and a height of approximately 7 inches functions satisfactorily. It has likewise been found that the use of two strips of inch-wide double-sided tape as the adhesive sections 72 provides an instrument pouch 70 that functions satisfactorily.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A surgical drape system for use in a procedure wherein a catheter is inserted into a vein or artery comprising:

a drape including a main sheet portion for covering at least a substantial portion of a patient having an aperture for providing access to an operative site; and an instrument pouch, including means for removably securing the pouch to the drape near the operative site, the pouch including means for removably receiving surgical tools and positioning catheters used during the surgical procedure with respect to the drape.

2. The surgical drape system of claim 1 wherein the pouch is substantially transparent.

3. The surgical drape combination of claim 1 wherein the means for removably receiving surgical tools includes at least one pocket defined by the pouch.

4. The surgical drape of claim 1 including at least one tab providing means for securing the catheter near the operative site.

5. The surgical drape of claim 1 wherein the aperture has an elliptical shape.

6. The surgical drape of claim 1 including an adhesive line, that substantially circumscribes the aperture, for securing the aperture around an operative site on the patient.

7. The surgical drape combination of claim 1 wherein the drape includes, secured to the main sheet portion, a pleated portion so constructed and arranged so as to drape along a patient's arm near the operative site.

* * * * *